United States Patent [19]

Hussman

[11] Patent Number: 5,437,280

[45] Date of Patent: Aug. 1, 1995

[54] MAGNETIC RESONANCE BREAST LOCALIZER

[76] Inventor: Karl L. Hussman, 501 Esplanade, #237, Redondo Beach, Calif. 90277

[21] Appl. No.: 124,690

[22] Filed: Sep. 20, 1993

[51] Int. Cl.$^6$ ............................................. A61B 5/055
[52] U.S. Cl. ............................ 128/653.2; 128/653.5; 128/749; 606/130
[58] Field of Search ............... 128/653.2, 653.5, 653.1, 128/749, 869, 846, 662.05, 915; 606/130

[56] References Cited

U.S. PATENT DOCUMENTS

| | | | |
|---|---|---|---|
| 4,981,142 | 1/1991 | Dachman | 128/749 |
| 5,024,229 | 6/1991 | Bryant et al. | 128/653.5 |
| 5,178,146 | 1/1993 | Giese | 128/653.5 |
| 5,285,787 | 2/1994 | Machida | 128/653.2 |

FOREIGN PATENT DOCUMENTS 4332531  11/1992  Japan .............................. 128/653.5

OTHER PUBLICATIONS

Kaiser, Werner A., Breast cancer diagnosis, Diagnostic Imaging, Sep., 1992.
Svane, G., Preoperative Marking of Breast Lesions, Acta Radiolagical Diagnosis, 1983.
Schnall, M. D., et al., A System for MR Guided Stereotactic Breast Biopsies and Interventions, Proceedings of the Twelfth Annual Scientific Meeting of the Society of Magnetic Resonance in Medicine, 1993, 1:163.
Liu, Haiying, et al., Fat Suppression, Proceedings of the Twelfth Annual Scientific Meeting of the Society of Magnetic Resonance in Medicine, 1993, 3:1188.
Hajek, Paul, et al., Localization Grid for MR-guided Biopsy, Radiology, 1987.
Steger, A. C., et al., Interstitial Laser Hyperthermia, Br Medical Journal, 1989, 299.
Castro, Dan, MRI Guided Interstitial Laser Phototherapy, Laryngoscope 102, Jan., 1992.
Ahlstom, K. Hakan, CT-guided Bone Biopsy, Radiology, 1993.
Harms, S. E., MR Imaging of the Breast, JMRI, Jan.-/Feb., 1993.
Heywang-Kobrunner, Sylvia, Breast Imaging Techniques, Current Opinion in Radiology, 1992.
Cosman, Eric, et al., Combined Use of a New Target-Centered Arc System, Proceedings of the Meeting of the American Society for Stereotactic and Functional Neurosurgery, Montreal 1987.
Langlois, S. L., et al., Carbon Localization, Australasian Radiology, Aug., 1991.
Harms, S. E. et al., MR Imaging of the Breast, Radiology, 1993.
Lagois, M. D., et al., Multicentricity in Breast Carcinoma, Pathology Annual, Appleton-Century-Crofts, New York, 1981.
Giorgi, C., et al., Reconstruction of Neuroradiological Data, applied Neurophysiology, 1987.
Heywang-Kobrunner, S. H., MRI of Breast Disease, Presented at the Twelfth Annual Scientific Meeting of the Society of Magnetic Imaging in Medicine, 1993.
Liu, H., et al., Biplanar Gradient Coil Imaging (abstract), JMRI, 1993.
Bown, S. G., Minimally Invasive Therapy in Breast Cancer (abstract), JMRI, 1993.
Derosier, C., MR and Stereotaxis, J. Neuroradiol, 1991.
Meyerowitz, Basil R, Drill Biopsy Confirmation, Arch Surg, vol. 111, Jul., 1976.

*Primary Examiner*—Ruth S. Smith
*Attorney, Agent, or Firm*—Timothy T. Tyson; Freilich, Hornbaker & Rosen

[57] ABSTRACT

Localizer embodiments (40, 140, 180, 240, 280) suitable for guidance of medical instrument tips (104) to a breast lesion (79) are provided. In one embodiment (40), the breast is closely fitted within a selected one of a plurality of sized MR transparent cups (44) to reduce movement during imaging and localization. A guide bore (60A) is selected from an array of bores and a medical instrument is guided therethrough in accordance with imaged spacings obtained with the aid of an MR visible coordinate system (46). A medical instrument (300) suitable for use with the localizers is also provided.

13 Claims, 10 Drawing Sheets

MAGNETIC RESONANCE BREAST LOCALIZER

TECHNICAL FIELD

The present invention relates generally to magnetic resonance mammography and more particularly to localizers for use therewith.

BACKGROUND OF THE INVENTION

Breast cancer is the leading cause of death from cancer among women in the western world and the leading cause of death in general among persons 35 to 55 years of age. Imaging modalities for detection of breast lesions include X-ray mammography, sonography, thermography, computed tomography, angiography and magnetic resonance imaging (MRI).

The application of MRI to the imaging, localization (guidance to a lesion site) and treatment of breast lesions is copiously described in the literature. MRI literature references include MR Mammography, Kaiser, Werner A., Springer-Verlag, Berlin Heidelberg, 1993; Kaiser, Werner A., MRM promises earlier breast cancer diagnosis, Diagnostic Imaging, September, 1992; Svane, G., Stereotaxic Technique for Preoperative Marking of Non-Palpable Breast Lesions, Acta Radiolagical Diagnosis, 1983; Schnall, M. D., et al., A System for MR Guided Stereotactic Breast Biopsies and Interventions, Proceedings of the Twelfth Annual Scientific Meeting of the Society of Magnetic Resonance in Medicine, 1993, 1:163; Liu, Haiying, et al., Fat Suppression with an Optimized Adiabatic Excitation Pulse, Proceedings of the Twelfth Annual Scientific Meeting of the Society of Magnetic Resonance in Medicine, 1993, 3:1188; Hajek, Paul, et al., Localization Grid for MR-guided Biopsy, Radiology, 1987; Steger, A. C., et al., Interstitial Laser Hyperthermia, Br Medical Journal, 1989, 299; Castro, Dan, Metastatic Head and Neck Malignancy Treated Using MRI Guided Interstitial Laser Phototherapy, Laryngoscope 102, January, 1992; Ahlstom, K. Hakan, CT-guided Bone Biopsy, Radiology, 1993; Harms, S. E., MR Imaging of the Breast, JMRI, January/February, 1993; Heywang-Kobrunner, Sylvia, Nonmammographic Breast Imaging Techniques, Current Opinion in Radiology, 1992; Cosman, Eric, et al., Combined Use of a New Target-Centered Arc System, Proceedings of the Meeting of the American Society for Stereotactic and Functional Neurosurgery, Montreal 1987; Langlois, S. L., et al., Carbon Localization of Impalpable Mammographic Abnormalities, Australasian Radiology, August, 1991; Harms, S. E., et al., MR Imaging of the Breast with Rotating Delivery of Excitation Off Resonance, Radiology, 1993; Lagois, M. D., et al., The Concept and Implications of Multicentricity in Breast Carcinoma, Pathology Annual, Appleton-Century-Crofts, New York, 1981; Giorgi, C., et al., Three-dimensional Reconstruction of Neuroradiological Data, applied Neurophysiology, 1987; Heywang-Kobrunner, S. H. MRI of Breast Disease, Presented at the Twelfth Annual Scientific Meeting of the Society of Magnetic Imaging in Medicine, 1993; Liu, H., et al., Biplanar Gradient Coil Imaging (abstract), JMRI, 1993; Bown, S. G., Minimally Invasive Therapy in Breast Cancer (abstract), JMRI, 1993; and Derosier, C., MR and Stereotaxis, J. Neuroradiol, 1991. The disclosures of the above cited references are hereby incorporated by reference and liberally drawn from for this background section.

MRI can be realized because atoms with an odd number of protons or neutrons possess an intrinsic rotation or "spin" that, for clarity, may be likened to the spinning of a top. The atomic nucleus also carries an electric charge, and the combination of spin and charge leads to the generation of a magnetic field around the particle. The nucleus, then, represents a magnetic dipole whose axis is directed parallel to the axis of spin.

In the absence of an applied external magnetic field, the orientations of the proton spin axes are distributed statistically in space, so the magnetic dipoles cancel out in terms of their external effect. When a patient is placed into a magnetic field, the magnetic moments become oriented either parallel or antiparallel to the external field. Each state has a different energy level, the parallel alignment being the more favorable state in terms of energy. To alter these different energy states, the energy difference must either be added to or absorbed from the system from the outside. This can be accomplished by the application of an electromagnetic pulse at the magnetic resonance (MR) frequency or "Larmor frequency". In a magnetic field of 1 Tesla, for example, the Larmor frequency is 42 MHz.

The applied radio frequency pulse tilts the spin axis of the protons out of alignment by an angle that depends on the amplitude and duration of the transmitted electromagnetic pulse. A 90° pulse is one that tilts the magnetization vector from the z axis to the xy plane, while a 180° pulse causes a complete inversion of the magnetization vector.

After the excitation pulse has passed, relaxation commences as the nuclei return to their original states. This realignment process is characterized by a relaxation time T1 and corresponds to the motion of an electric charge in a magnetic field. As a result, the relaxation process causes the emission of an electromagnetic signal (the MR signal) from the nuclei that can be detected with special antennas (coils).

When the resonance frequency is applied to the sample as a 90°pulse, the pulse not only tilts the magnetic moment 90° but also tends to align the spin axes in the direction of the rf pulse. The angle of the spin axes is called the "phase". When the rf pulse ceases, the individual spins immediately begin to go out of phase. This "dephasing" process is called spin-spin relaxation and is characterized by a T2 relaxation time. The spin-lattice or T1 relaxation time describes the return of the magnetic moment to alignment with the external magnetic field. Both processes occur simultaneously in the same nucleus. Characteristic T1 values in biologic tissues range from 0.5 to 2 seconds and T2 values from 10 to 200 milliseconds.

By modifying the amplitude and duration of the applied rf pulses, an investigator can manipulate the alignment of the nuclear spins in varying degrees and for varying lengths of time. Accordingly, the MR signals generated by the tissue relaxation process vary greatly depending on the type of excitation pulses that are applied. The basic pulse sequences in clinical use include spin-echo, inversion recovery, gradient echo and fat suppression. Specialized pulse sequences under these general types include FLASH, FISP, RODEO and SNOMAN.

Image plane selection (slice selection) is accomplished by superimposing a linear gradient field upon a static magnetic field. Because the gradient field increases linearly in one direction, e.g., along the z axis, there is only one site at which the resonance or Larmor frequency condition is met. The bandwidth of an applied rf pulse and the steepness of the gradient determine the thickness of the tissue slice from which MR signals emanate. When two additional gradient fields are applied in the x and y directions, frequency or phase information can be assigned to different points within the selected plane.

A complete pulse sequence yields a raw-data image called a hologram. A 2-dimensional Fourier transform is applied to the raw data to construct the final image. Through the switching of magnetic gradients, sectional images can be constructed on a coronal, axial or sagittal plane or in any oblique orientation desired (coronal, axial and sagittal planes are respectively those dividing the frame into front and back portions, those dividing the frame into right and left portions and those dividing the frame into upper and lower portions).

Components of an MR unit include a primary magnet, shim coils whose current supply is computer controlled to produce the desired field homogeneity, gradient coils to generate linear gradient fields, an rf coil for transmitting the rf pulses and receiving the MR signals (the signals may be received through the transmitting coil or a separate receiving coil), a computer for control of data acquisition, imaging parameters, and analysis and data storage media.

The rf excitation signal and the MR signal emitted by relaxing nuclear spins are respectively transmitted and received with rf coils types that include surface coils, whole-volume coils (in solenoid, saddle and birdcage configurations), partial-volume coils, intracavitary coils and coil arrays.

Breast coils are typically whole-volume solenoids used both for transmission and receiving. Such coils are especially suited for imaging frame regions that are perpendicular to the magnet aperture, e.g., breasts, fingers. They include square 4 pole resonators that can be inserted over the breast during imaging and Helmholtz pair resonators. Pairs of breast coils are often coupled to allow imaging of both breasts, e.g., see Model QBC-17 Phased Array Breast Coil, MRI Devices Corporation, 1900 Pewaukee Road, Waukesha, Wis.

The MR signal intensity varies exponentially with T1 and T2. Thus, a substance that alters the tissue relaxation times can be a potent image contrast enhancer. Gadolinium-diethylene triamine-pentaacetic acid (Gd-DTPA) is particularly suitable for producing contrast enhancement. Enhancement following injection seems to correlate with the vascularization of the lesion and the intense MR signal enhancement in carcinomas may be due to their increased vascular density.

Dynamic imaging involves repetitive imaging of the same slices before and after injection of Gd-DPTA. Dynamic, contrast-enhanced MR imaging has been found to be especially effective in differentiating benign from malignant lesions. MR signal increases (typically within the first minute after injection) can help differentiate carcinoma from benign breast lesions such as fibroadenoma, proliferative mastopathy, cysts, scars and mastopathies.

Numerous investigations and tests have demonstrated the high sensitivity (proportion of people having a disease that are so identified by a test) and specificity (proportion of people free of a disease that are so identified by a test) of MR imaging and its ability to detect even small cancers, e.g., 3-5 millimeters. However, successful imaging of breast lesions must be accompanied by effective guidance of medical instruments to the lesion site to facilitate diagnosis and treatment.

Figure 1A:
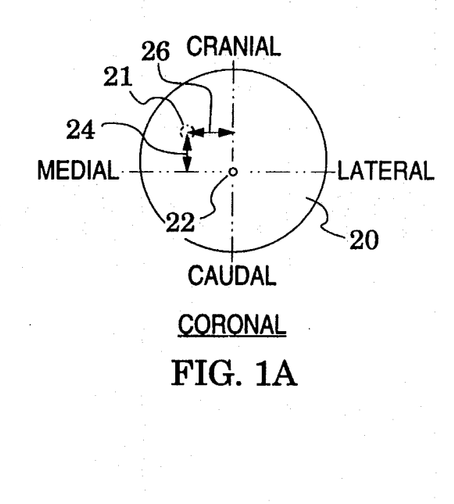
FIGS. 1A, 1B and 1C illustrate medical coordinates relative to a breast.
Figure 1B:
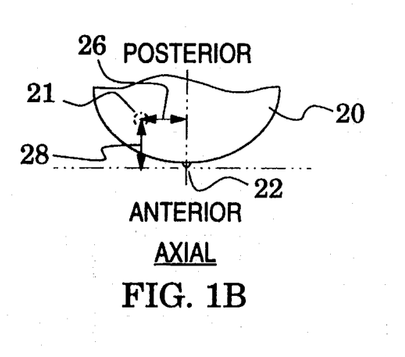
Figure 1C:
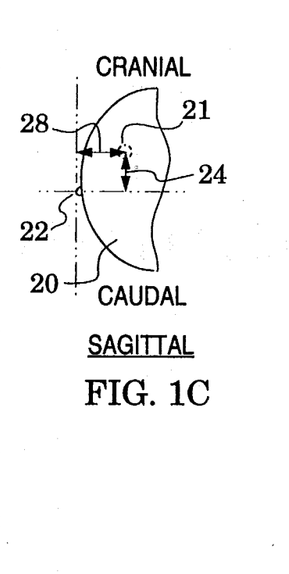

Accurate guidance is especially difficult in breasts because they lack rigid structure as, for example, in the cranium and can assume numerous configurations. FIGS. 1A, 1B and 1C are respectively front, top and side views of a breast 20 and illustrate how the location of a breast lesion 21 is typically described in relation to a coordinate system centered on the breast nipple 22. In these views, the lesion 21 exhibits cranial spacing 24, medial spacing 26 and posterior spacing 28 from the nipple 22. However, it is apparent that if the breast 20 were allowed to assume a configuration different from that of FIG. 1, these spacings would no longer accurately describe the lesion location. Thus, imaging and localization procedures are preferably completed without disturbing the breast position therebetween so that the imaging spacings used for localization are not corrupted.

Non-invasive localization or guidance techniques include measurement of the spacing between the lesion and the nipple and between the lesion and the overlying skin surface and transposition of the measurements to the breast surface where the calculated site is marked as a guide for a surgeon. Because of the considerations described above, non-invasive techniques generally permit only approximate guidance.

Invasive localization techniques often include apparatus for reducing breast movement and/or providing an MR visible coordinate. For example, perforated compression plates having rectangular apertures therein and an image visible coordinate system are described in Svane and Schnall in the above incorporated references. Gd-DTPA filled polyethylene tubes arranged in a grid and taped to an abdomen as a localization aid are described in Hajek in the above incorporated references.

Invasive treatment techniques include the insertion of a carbon trail leading to the lesion vicinity with a carbon trail injector as described in Svane and Langlois in the above incorporated references. The carbon trail serves as a marker to guide a surgeon to the lesion. Hook-wires are inserted to the lesion vicinity for the same purpose. They are typically removed during surgery. Introducing a fiber optic to the lesion vicinity for treatment with laser energy is described in Bown and Steger in the above incorporated references (interstitial laser photocoagulation or ILP in Bown; interstitial laser hyperthermia in Steger). In these treatment techniques, the laser fiber is typically passed through a thin needle to the lesion site.

Preferably, laser therapy is performed with the breast in a relaxed position to avoid forcing (as in compression techniques) a lesion proximate to the skin surface or urging separate lesions together thus losing spatial differentiation. In the first case, skin tissues may be destroyed and in the second case, healthy tissue between the lesions may unnecessarily be removed.

Other well known invasive procedures include the introduction of a needle for aspiration biopsy, a rotex screw biopsy needle within a cannula and a trocar within a cannula. In general, the goal of successful localization is the guidance of a medical instrument tip to the lesion site determined by imaging.

Because of the large magnetic fields involved in MR imaging, it is highly desirable that only nonferromagnetic materials be introduced within the magnetic fields. In addition, some materials can produce imaging artifacts (other sources of imaging artifacts include patient movement, heart movements, and chemical shifts due to resonance frequency difference of water and fat protons). Materials that do not exhibit nuclei relaxation will not appear on the MR image. On the other hand, if it is desired that a structure appear on the MR image, the material of that structure should exhibit nuclei relaxation.

Materials that do not cause imaging artifacts nor appear on the MR image shall hereinafter be called MR transparent while materials that are intended to appear on the MR image shall hereinafter be referred to as MR signal-producing. An example of an MR transparent material is polycarbonate. An example of an MR signal-producing material is Gd-DTPA contained in an MR transparent material.

SUMMARY OF THE INVENTION

The present invention is directed to a localizer for guidance of the tip of a medical instrument to a breast lesion identified by magnetic resonance (MR) imaging. The localizer enables breast imaging and medical instrument guidance relative to an MR visible coordinate system.

Apparatus in accordance with the invention are characterized by an MR visible coordinate system representing points within an imaging space, a breast positioning device positioned within that imaging space and at least one array of bores operatively arranged with the coordinate system for guiding the tip of a medical instrument proximate to any point defined within the imaging space by MR imaging.

In a preferred embodiment, the breast positioning device includes a breast shaped cup. In another preferred embodiment, a plurality of breast shaped cups of different sizes is provided. One of the cups may be selected in accordance with the volume of the breast to be imaged. In another preferred embodiment, the breast positioning device includes an inflatable bladder to position the breast within a frame.

In a preferred embodiment, the MR visible coordinate system includes markers having lumens defined within a frame and an MR signal-producing material contained in the lumens.

In accordance with a feature of the invention, bore arrays are spatially interleaved to increase their resolution capability.

The novel features of the invention are set forth with particularity in the appended claims. The invention will be best understood from the following description when read in conjunction with the accompanying drawings.

DESCRIPTION OF PREFERRED EMBODIMENTS

Figure 2:
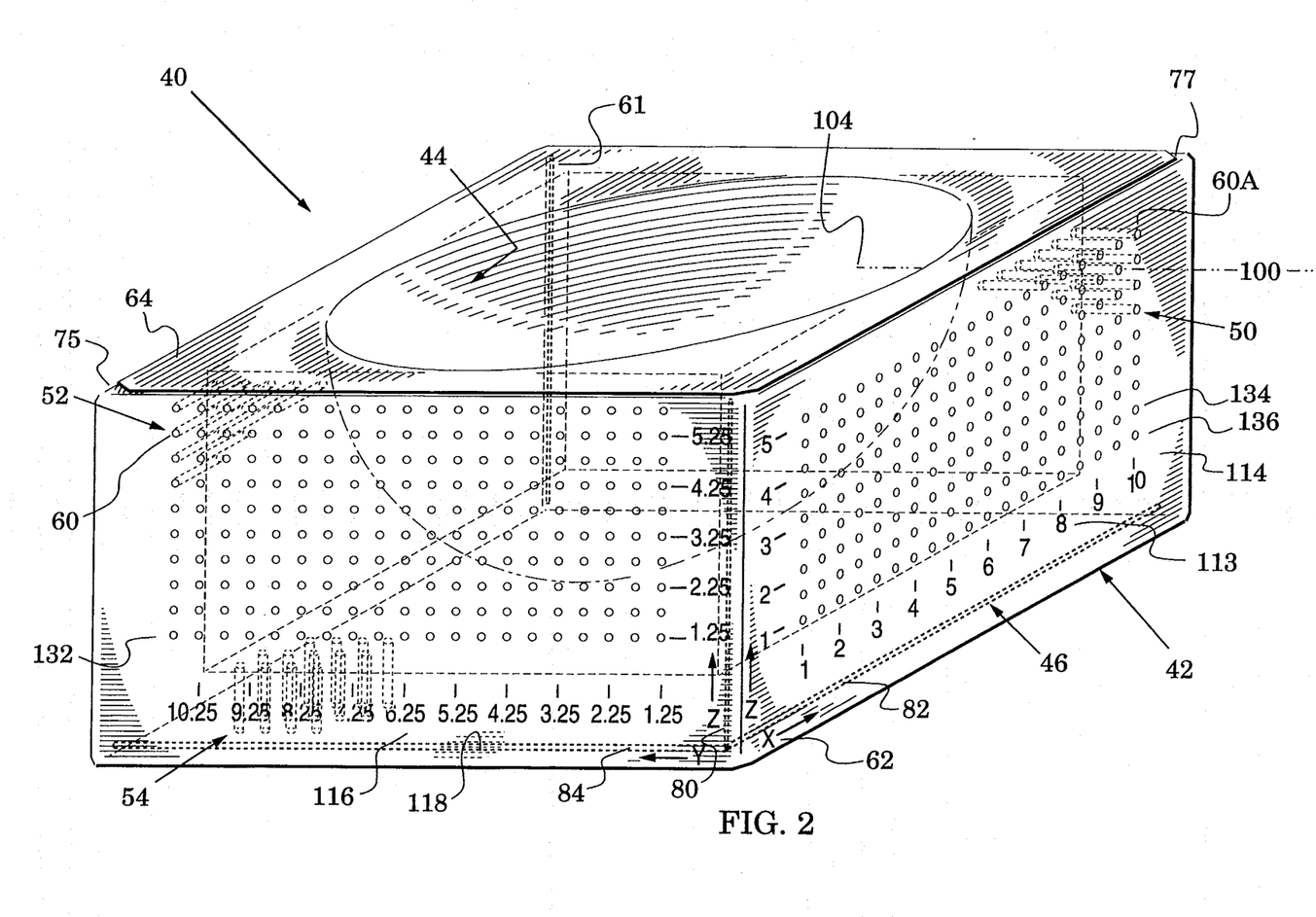
FIG. 2 is an isometric view of a preferred localizer embodiment, in accordance with the present invention.
Figures 3A, 3B:
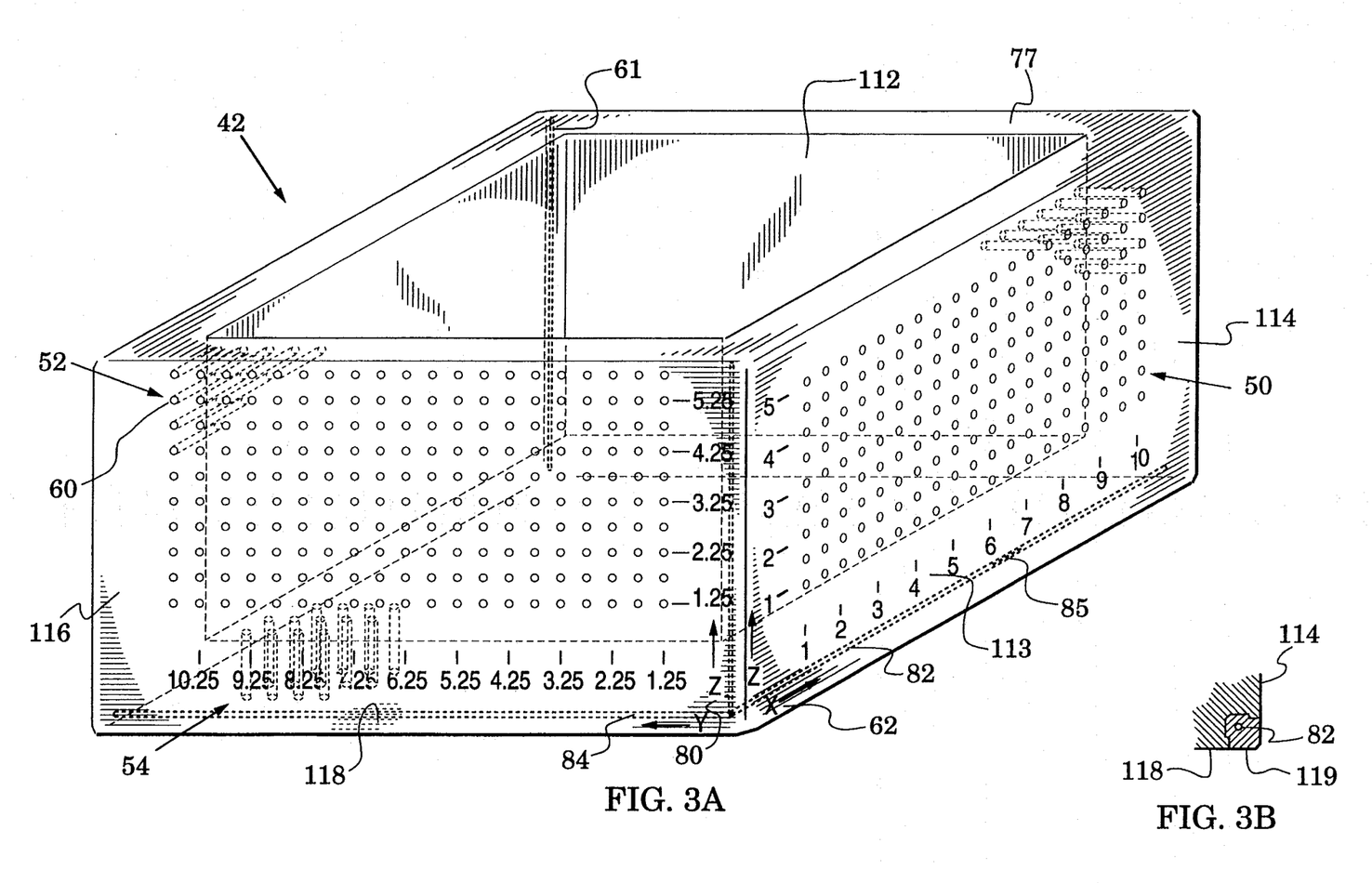
FIG. 3A is an isometric view of the frame in the localizer of FIG. 2.
FIG. 3B is a partial sectional view of an alternative embodiment of FIG. 3A.
Figure 4:
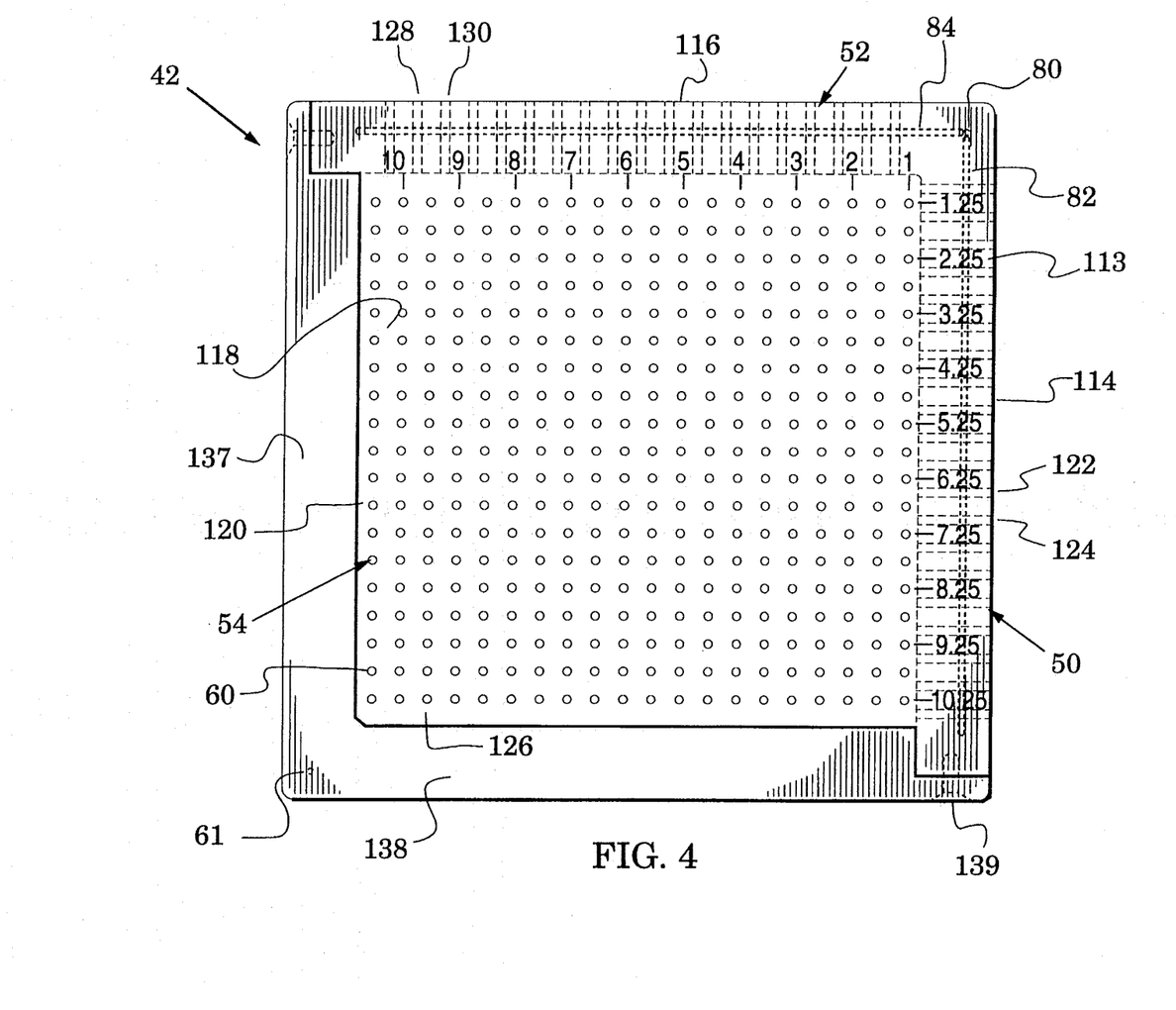
FIG. 4 is a bottom plan view of the localizer of FIG. 2 including removable walls.

FIG. 2 is an isometric view of a preferred localizer embodiment 40, in accordance with the present invention, having a frame 42 and a cup 44 carried by the frame. FIGS. 3A and 4 are respectively isometric and bottom plan views of the frame 42 and FIG. 5 is an isometric view of the cup 44.

As shown in these views, the frame 42 includes an MR signal-producing Cartesian coordinate system 46 having x, y, and z coordinate axes markers 82, 84, and 80, respectively, and bore arrays 50, 52 and 54 aligned therewith (the array 54 is only partially shown in FIGS. 2, 3A for clarity of illustration). Each of the bore arrays includes a plurality of bores 60 defined by the frame 42. As an operational aid in its use, the localizer includes an MR signal-producing reference axis marker 61 and coordinate axes identifying indicia 62.

Figure 5:
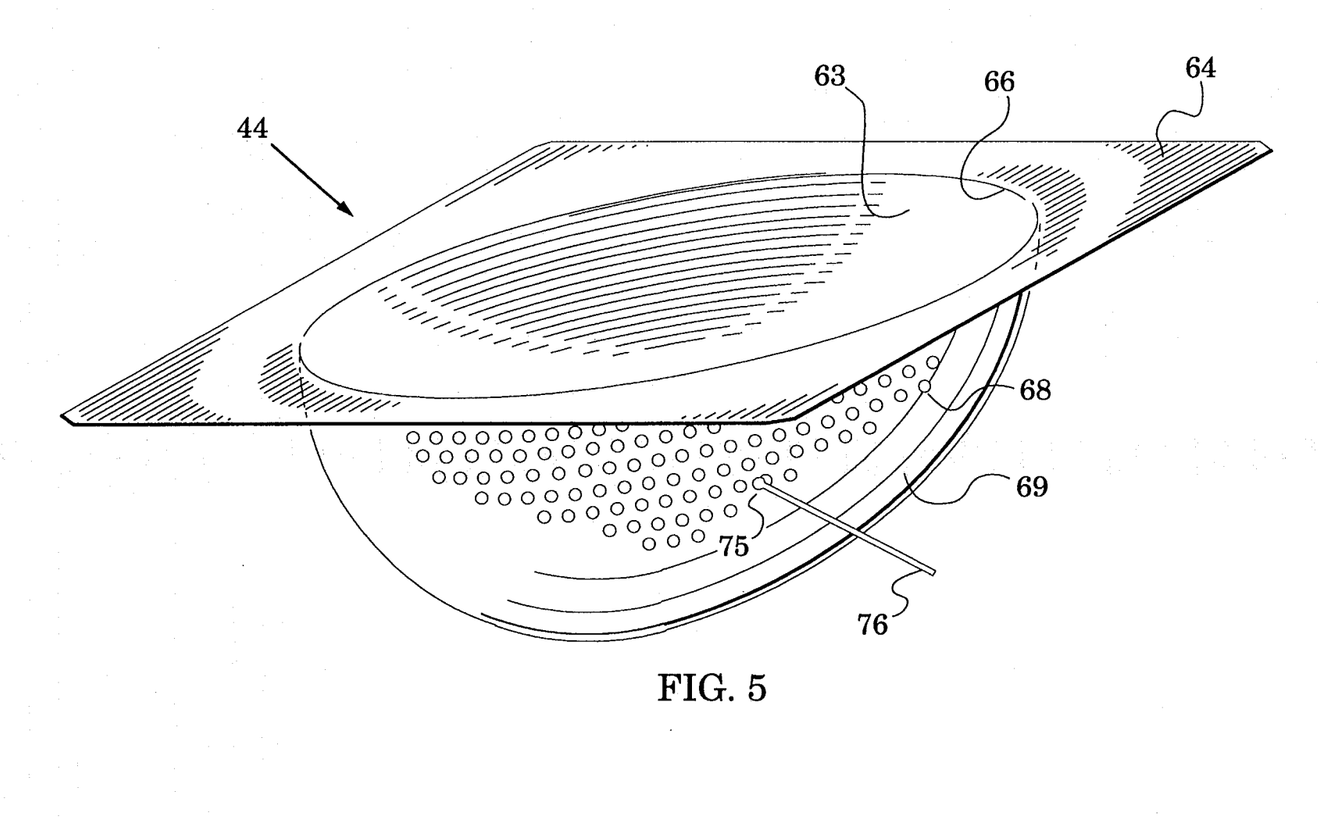
FIG. 5 is an isometric view of the cup in the localizer of FIG. 2.

As specifically shown in FIG. 5, the cup 44 has an inner surface 63 which is shaped and configured to closely receive a breast therein. In addition, the cup 44 defines a flange 64 extending from the cup rim 66 and a plurality of apertures 68 in the cup wall 69. For clarity of illustration, a limited number of apertures are shown but the apertures 68 may extend over the entire cup wall 69. The cup 44 is formed of a thin nonferromagnetic, MR transparent material (i.e., one that does not produce an MR signal nor an MR artifact as defined in the background section) which is rigid enough to stabilize the breast therein but which permits free transgression of a needle tip at any point, e.g., plastic. In accordance with a feature of the invention, a plurality of cups 44 are provided, each having a different volume defined between the inner surface 63 and the plane of the cup rim 66.

Figure 6:
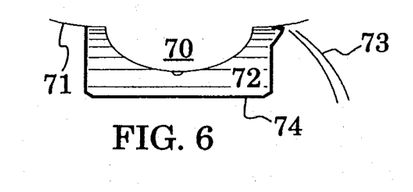
FIG. 6 is a schematic view of a breast volume measurement method.

In use of the cups 44, the volume of a breast 70 to be MR imaged within the localizer 40 would be measured by insertion up to the chest wall 71 in a liquid 72 as shown in the schematic view of FIG. 6. The liquid 73 displaced from the container 74 is an accurate measure of volume of the breast 70. A cup 44 would then be selected from the plurality of cups in accordance with the measured breast volume.

The fit between the breast and the selected cup is further enhanced by the contour of the inner surface 63 which is generally breast shaped to define a conforming surface. For example, the inner surface may be formed in accordance with molds of actual breasts or formed to define a parabolic shape.

To further minimize movement of the breast surface relative to the cup wall 69, a surgical grade adhesive 75, e.g., dimethylpolysiloxane, may be applied to both through the apertures 68. For example, the adhesive could be applied by an applicator 76 as illustrated in FIG. 5. Other effective application methods may be used, e.g., spraying through a thin tube. The adhesive can be removed later with medical grade solvents, e.g., trichlorotrifluoroethane.

The breast and cup 44 are then arranged to have the cup 44 carried by the frame 42 as shown in FIG. 2 with, preferably, the medical grade adhesive 75 also applied between the flange 64 and a lip 77 defined by the frame 42 and between the flange 64 and the chest wall surrounding the breast. The localizer 40 and patient are then situated appropriately within an MR unit for imaging of the breast. Typically in this process, the patient lies in a prone position within the MR unit.

MR breast imaging would then be conducted as briefly described above in the background section and as well known to those skilled in the art. This imaging typically includes a fat suppressed 3D contrast-enhanced pulse sequence followed by maximum-intensity-projection (MIP) and rotational reconstruction of lesion coordinates. If the patient has a breast lesion, the imaged lesion 79 would appear on the MR computer display along with the MR visible coordinate system 46 of FIG. 2 which serves to define points in an imaging space within the coordinate system. This is illustrated in FIGS. 7A and 7B.

Figure 7A:
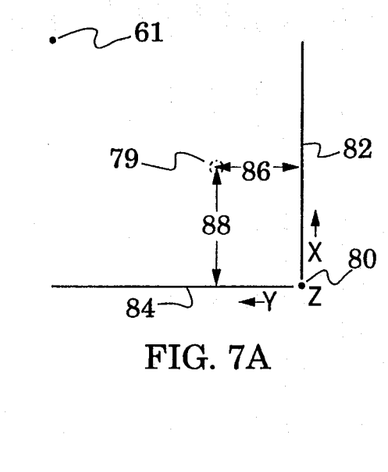
FIG. 7A is an MR computer display of an imaged lesion and coordinate system.

FIG. 7A represents a zero degree MIP projection of the contrast enhanced lesion 79 within the MR visible coordinate system (46 of FIG. 2) as viewed from above; the x and y coordinate axes markers 82, 84 are displayed en-face while the reference axis marker 61 and z coordinate axis marker 80 appear as points confirming exact zero degree rotation of the MIP projection. The x and y lesion coordinates 88, 86 are determined by measurement of perpendiculars to the y and x axes respectively.

Figure 7B:
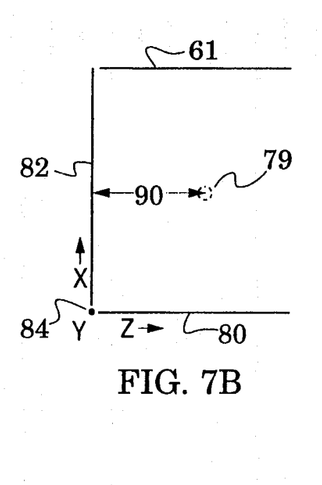
FIG. 7B is another MR computer display of an imaged lesion and coordinate system.

FIG. 7B represents a 90 degree rotation of the MIP projection of FIG. 7A towards the right, corresponding to a left-lateral view of the coordinate system (46 of FIG. 2). This projection displays the x and z coordinate axes markers 82, 80 and the reference axis marker 61 en-face; the y axis marker 84 appears as a point confirming exact 90 degree rotation. The z lesion coordinate 90 is determined by measurement of a perpendicular to the x axis. For unambiguous identification of coordinate axes, an MR visible marker may be placed proximate to either the x or y axes. The reference axis marker 61, in conjunction with the z axis axis marker 80, defines the position of the lesion on individual coronal images of the contrast-enhanced fat-suppression MR study, and aids the MR technologist in positioning of slices.

With the x, y, z coordinates 88, 86, 90 determined, the nearest corresponding bore 60 can be chosen from any of the bore arrays 50, 52, 54. For example, if bore 60A in the bore array 50 meets this criteria, a medical instrument, schematically indicated by broken line 100, would then be guided through bore 60A until its tip 104 reaches the point represented by the coordinates 88, 86, 90.

Thus, within the resolution limits of the bore spacings of the array 50, the instrument tip 104 has been guided to the lesion site. The localization described above is preferably completed directly after imaging and without movement of the patient and localizer 40. The lesion 79, therefore, has not been moved relative to the coordinate system 46 during imaging and subsequent guidance of the medical instrument tip 104 to the lesion site. The cup wall 69 is preferably formed as thin as possible to allow easy instrument penetration to minimize disturbance of the breast subsequent to establishing lesion spacings. If desired, application of adhesive between the breast and cup wall 69 described above may effectively be restricted to those wall apertures 68 surrounding the bore selected in accordance with the imaged lesion spacings.

Returning attention now to details of the frame 42 as shown in FIGS. 3A and 4, the orthogonal Cartesian coordinate axes markers 80, 82 and 84 (which may be considered to be respectively z, x and y axes) are lumens (with the same reference number) defined by the frame 42 and filled with an MR visible material 85, e.g., Gd - DPTA liquid or other MR signal-producing material (which may be semisolid). The material in the lumens should be one that will produce an MR signal in all anticipated pulse sequences of the MR imaging. For example, mineral oil may produce an MR signal in many pulse sequences but, as opposed to Gd - DPTA, will not produce an MR signal in fat suppression sequences such as RODEO. The lumen of the reference marker 61 is diametrically opposed to (relative to the cup 44) and parallel with the lumen of the x coordinate axis marker 80 to define another coordinate axis as an aid in identifying the cup area on the MR computer display.

In the embodiment 40, the frame 42 is formed of a nonferromagnetic, MR transparent material and defines a recess 112 to receive the cup 44. The bore arrays 50, 52 and 54 are arranged orthogonally and aligned in operative association with the coordinate axes markers 80, 82 and 84. The diameter of the bores 60 is selected to closely receive the instrument therethrough without excessive binding. Bore diameter and bore length are chosen to minimize deviation of the instrument tip 104 from the bore axis as the instrument passes through the bore (it should be apparent that in all embodiment figures, only a few bores of each array have been shown completely for clarity of illustration).

As an aid in selection of an appropriate bore 60 to select in guiding the instrument 100 in accordance with the MR computer display of FIG. 7, array indicia 113 are provided on the frame faces 114, 116 and 118. These indicia indicate spacings of array rows and columns from the coordinate axes markers 80, 82 and 84 compatible with the spacing units used by the computer display.

Although the frame 42 is shown in FIGS. 2-4 to be integral, it preferably has removable lumens so that in cleaning of the localizer, the MR signal-producing material in the lumens is not subjected to excessive temperatures or other cleaning conditions that might degrade its performance. Accordingly, the frame may include removable lumens as shown, for example, in the partial sectional view of FIG. 3B where the frame is relieved along the frame faces 114, 118 and parallel to the lumen of marker 82 to slidingly receive a conformingly shaped strip 119 which defines the lumen of marker 82.

To increase the resolution capability of available guide bores, the spacing between the bores 60 in each array is selected to be as narrow as is practicable with the material and fabrication technique available. In accordance with a feature of the invention, after this spacing has been narrowed as far as is practicable, the arrays 50, 52 and 54 are arranged to be spatially interleaved, e.g., to each have elements such as rows and columns spatially interleaved with elements of other arrays. For example, as seen in FIG. 4, row 120 of the array 54 is interleaved between columns 122 and 124 of the array 50 and column 126 is interleaved between columns 128 and 130 of the array 52. Similarly, row 132 of array 52 is interleaved with rows 134, 136 of the array 50 as shown in FIG. 2.

The imaging displays shown in FIG. 7 may provide lesion spacings from all marker of coordinates, i.e., from marker 80, 82, pair 80, 84 and markers 82, 84. An appropriate set of these spacings that most closely guides the instrument tip 104 to the lesion site can be selected. The array interleaving described above presents a greater resolution to this selection than would be otherwise be available.

With many medical instruments, e.g., a biopsy needle, the instrument can be withdrawn from the breast through the selected bore 60. However, some instruments can not, e.g., a hook-wire. Accordingly, FIG. 4 illustrates an embodiment variation in which the frame walls 137, 138 that respectively oppose the faces 114, 116 are separate and removable from the remainder of the frame. Thus after localization, the breast and attached hook-wire may be moved away from the faces 114, 116 so that the free end of the hook-wire can be withdrawn from its enclosing bore. The walls 137, 138 may be attached to the remainder of the frame 42 with conventional fasteners, e.g., screws 139, or with any well known quick-disconnect fastener of suitable nonferromagnetic and MR transparent material.

Figure 8:
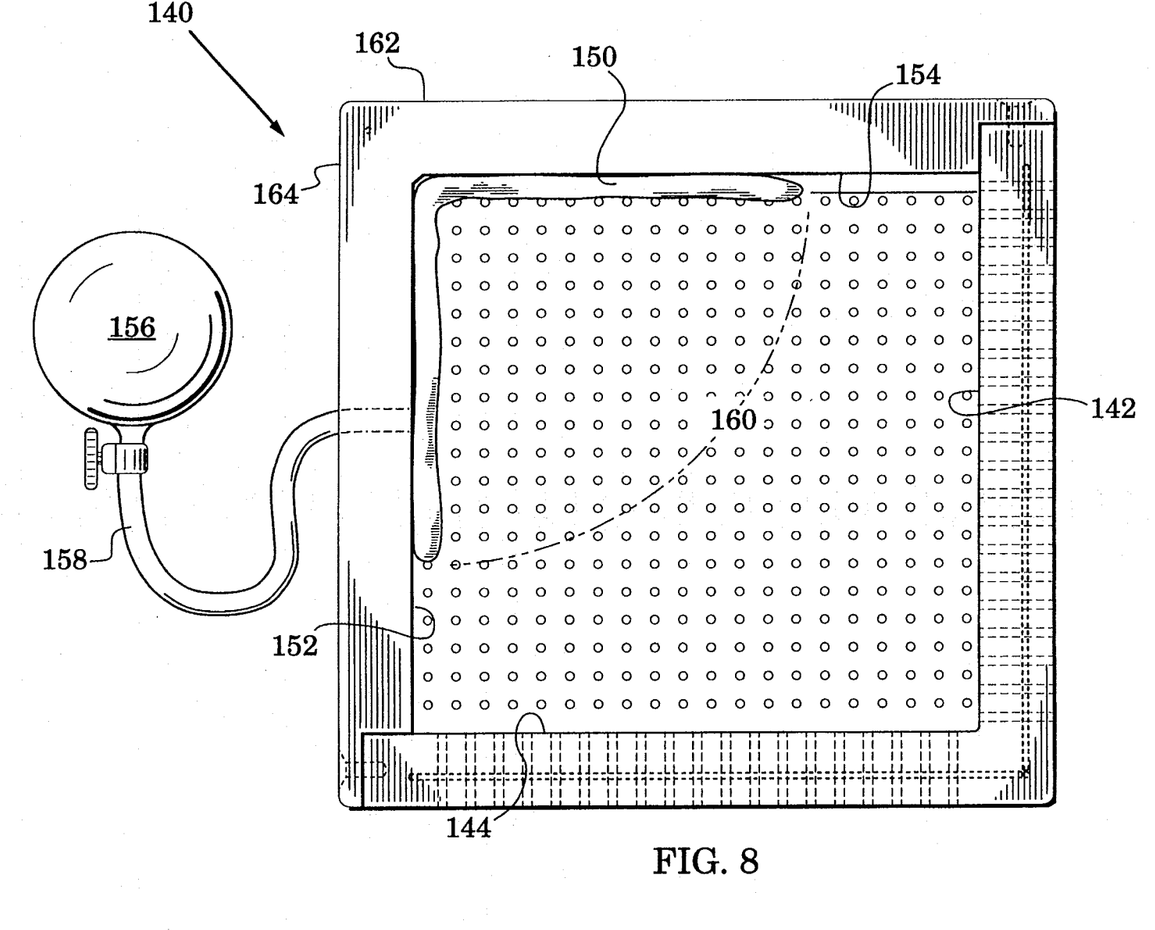
FIG. 8 is a top plan view of the localizer of FIG. 2 including removable walls and an inflatable bladder.

The top plan view of FIG. 8 illustrates another preferred localizer embodiment 140. The localizer 140 is similar to the localizer 40 of FIG. 2 but replaces the selected cup 44 with a combination of the interior frame faces 142, 144 that form the recess 112 and an inflatable bladder 150 disposed adjacent the respectively opposite interior faces 152, 154. By use of a resilient ball 156 and connecting tube 158, an operator can expand the bladder 150 as shown by the phantom line 160 to enclose and support the breast between the bladder 150 and the interior faces 142, 144. Of course, all materials of the bladder and associated structure preferably are nonferromagnetic and MR transparent. The embodiment 180 shows removable walls 162, 164 similar to the removable walls of FIG. 4.

Figure 9:
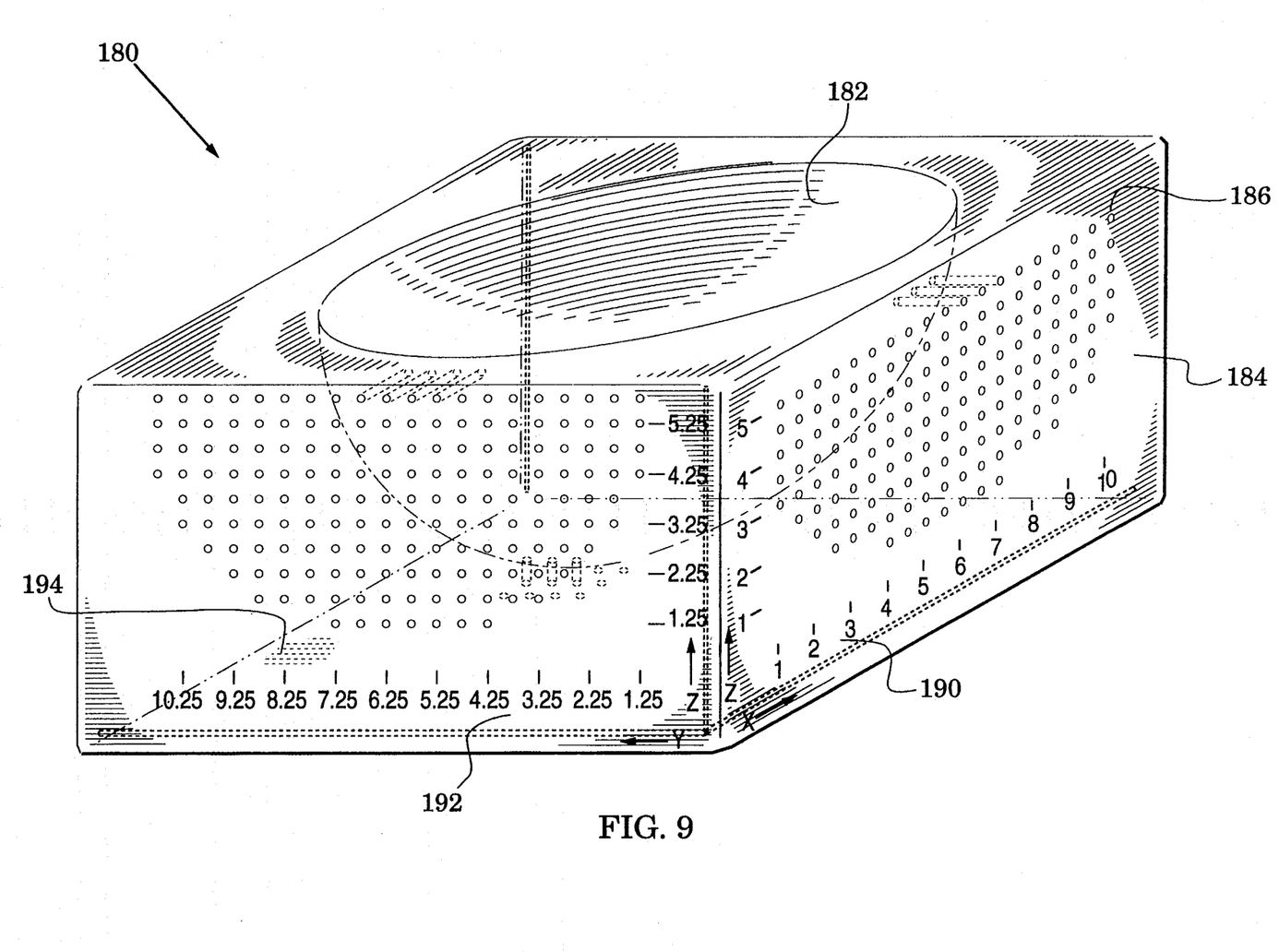
FIG. 9 is an isometric view of another preferred localizer embodiment.

Another preferred localizer embodiment 180 is illustrated in the isometric view of FIG. 9. The localizer 180 is similar to the localizer 40 but replaces the selected cup 44 with an interior breast receiving surface 182 defined by the frame 184. Thus all bores 186 are from the faces 190, 192 and 194 to the interior surface 182. The embodiment 180 permits the use of a simple frame to perform localization.

Figure 10:
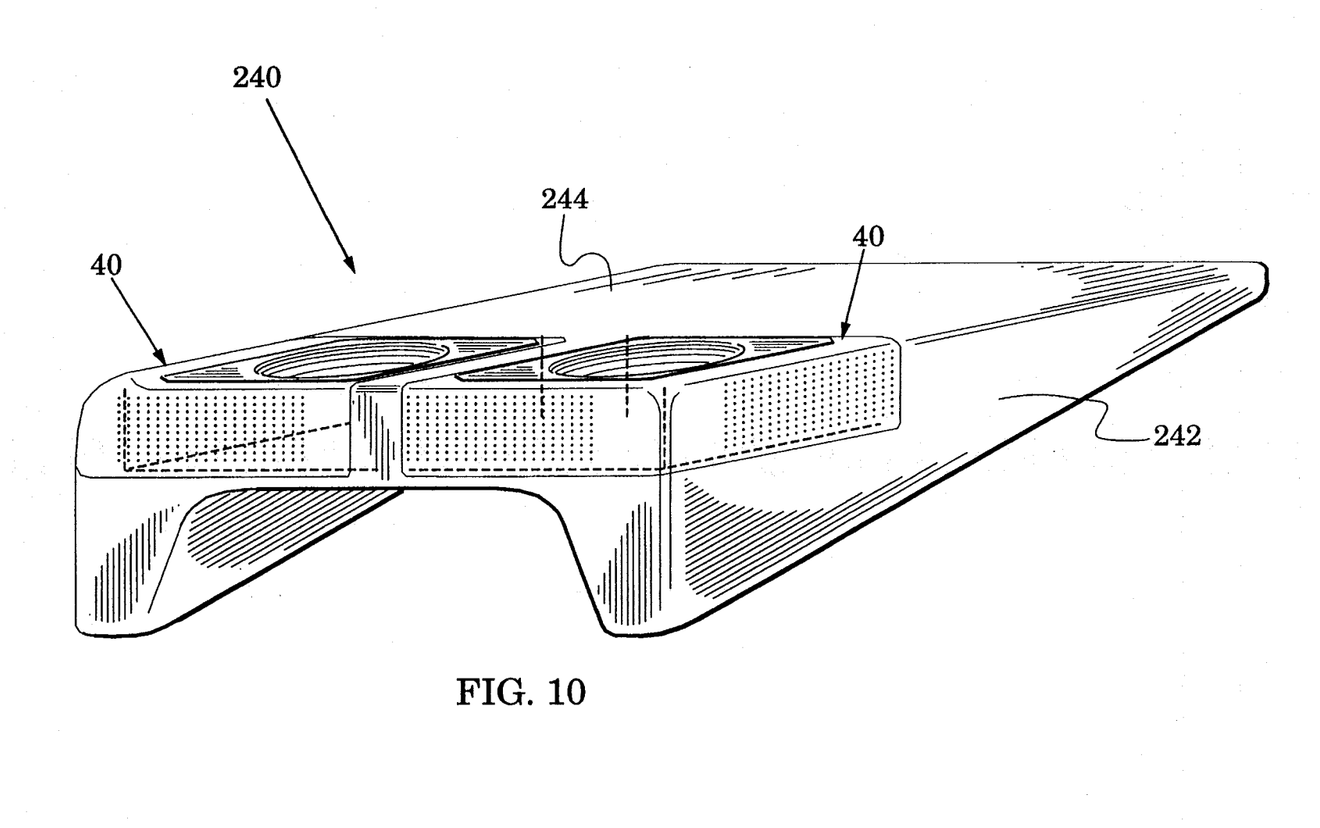
FIG. 10 is an isometric view of another preferred localizer embodiment.

The teachings of the invention can be extended to another preferred localizer embodiment 240 illustrated in FIG. 10. The embodiment 240 includes a housing 242 configured to present an inclined surface 244 against which a patient may comfortably be supported in a prone position within the MR unit. The housing 242 is configured to receive a pair of spaced localizers 40 (as shown in FIG. 2) so as to present them along the plane of the inclined surface 244. In use, the patient's breasts are received in the localizers 40 as described above. Imaging and guidance of medical instruments is then conducted as described above relative to other embodiments.

Figure 11:
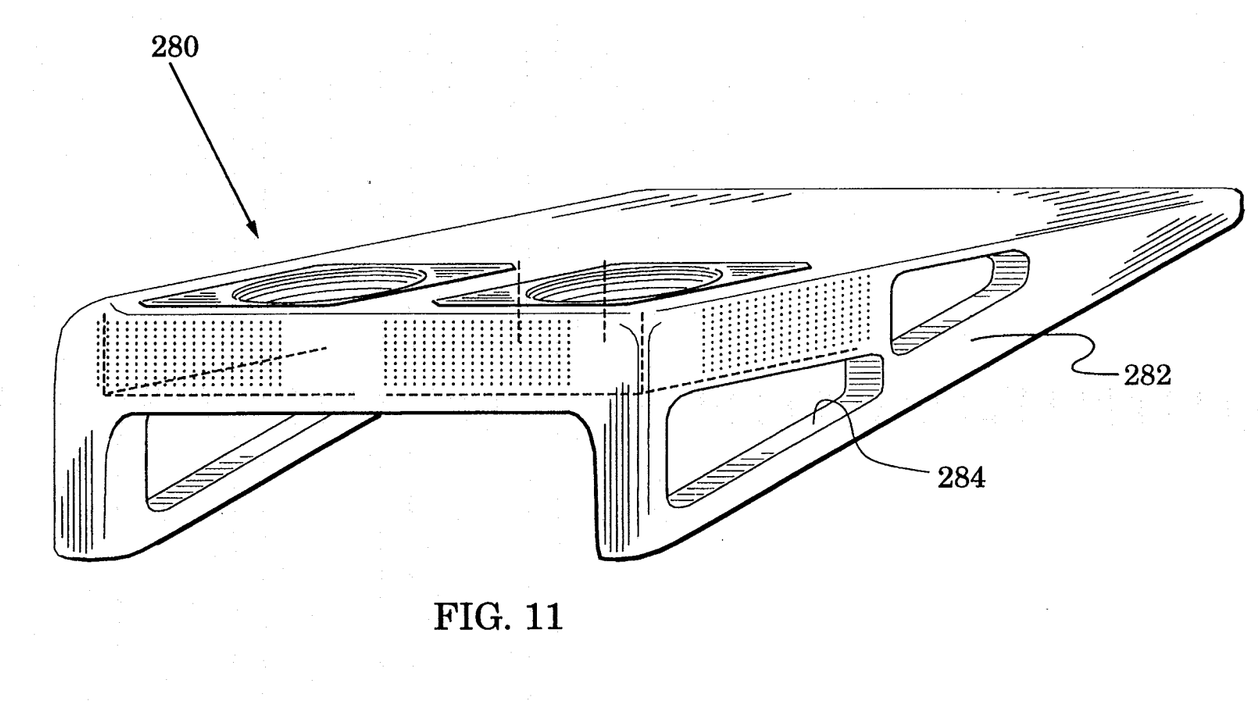
FIG. 11 is an isometric view of another preferred localizer embodiment.

Another preferred localizer embodiment 280 is shown in FIG. 11. The embodiment 280 is similar to the embodiment 240 but its housing 282 incorporates the localizers 40 of the embodiment 240 into a single unit, i.e., the localizers are not removable. The housing 282 also indicates exemplary reliefs 284 that may be designed thereinto by those skilled in the imaging art to accommodate breast imaging coils.

Figures 12A, 12B:
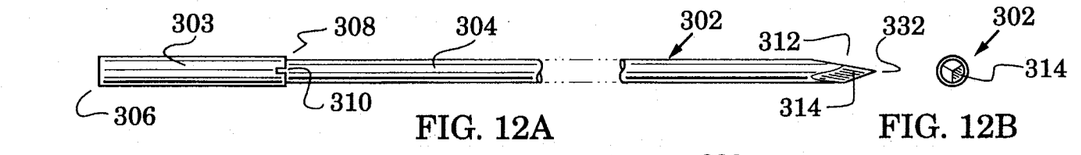
FIG. 12A is a side view of a preferred trocar embodiment for use with the preferred localizer embodiments.
FIG. 12B is an end view of the trocar of FIG. 12A.
Figures 14A, 14B:
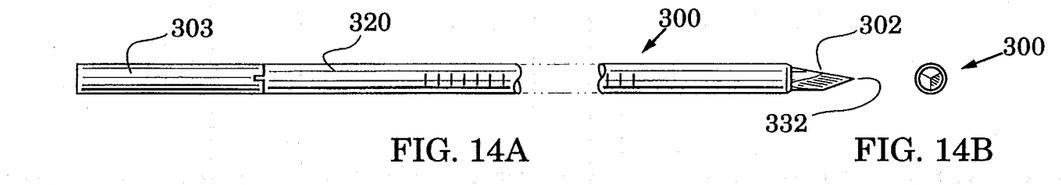
FIG. 14A is a side view of a the trocar of FIG. 12 received within the cannula of FIG. 13.
FIG. 14B is an end view of the structure of FIG. 14A.
Figures 15A, 15B:
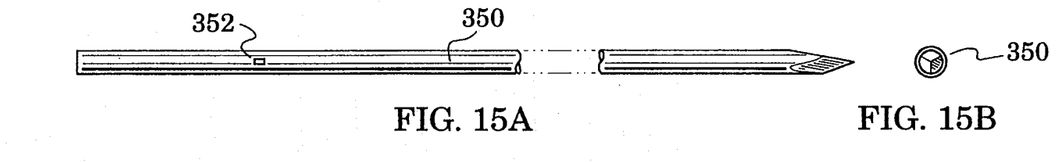
FIG. 15A is a side view of another preferred trocar embodiment.
FIG. 15B is an end view of the trocar of FIG. 15A.
Figure 16A:
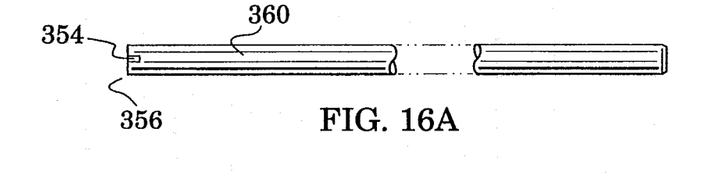
FIG. 16A is a side view of another preferred cannula embodiment for use with the trocar embodiment of FIG. 15.
Figure 16B:
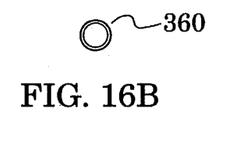
FIG. 16B is an end view of the cannula of FIG. 16A.

As mentioned above, it is desirable to minimize movement of either the breast or its supporting structure, e.g., the cup 44 of FIG. 2, during imaging and localization. In particular, such movement is preferably minimized during insertion of medical instruments for guidance to lesion sites. Accordingly, a preferred trocar/cannula embodiment 300, for use with the localizers disclosed herein, is shown in FIGS. 14A, 14B to have a trocar 302 and a cannula 302. In particular, the trocar 302 is shown in the side and end views respectively of FIGS. 12A, 12B. The trocar 302 has a cylindrical stem 304 that enlarges proximate a driving end 306 to an enlarged portion 303 which defines a stop 308 and, within the stop, a notch 310. The end 312 of the trocar terminates in a tip 332 which is preferably coaxial with the stem 304. It may be shaped with axially symmetric facets to minimize cutting forces that would force the trocar away from a penetration axis such as the axis of the bores of the localizer. For example, the embodiment 302 defines three cutting facets 314.

Figures 13A, 13B:
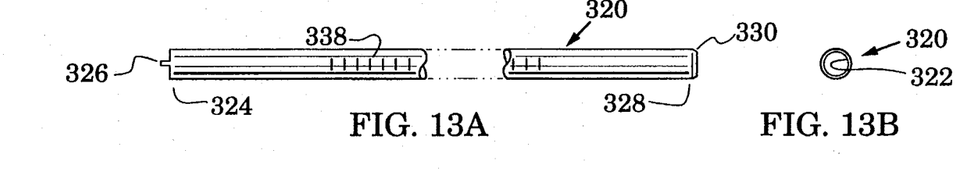
FIG. 13A is a side view of a preferred cannula embodiment for use with the trocar embodiment of FIG. 12.
FIG. 13B is an end view of the cannula of FIG. 13A.

The embodiment 300 also includes a cannula 320 shown in the side and end views respectively of FIGS. 13A, 13B to have a passage 322 dimensioned to closely receive the trocar 302 for rotation therein. On a driven end 324, the cannula defines a tab 326 which is dimensioned to be received in the notch 310 of the trocar 302. On a leading end 328, the cannula defines an annular bevel 330 to minimize penetration resistance. Both trocar and cannula are formed from a nonferromagnetic and non artifact-producing material, e.g., titanium or stainless steel with a high nickel content, to be substantially MR transparent.

When the trocar 302 is received in the cannula 320 to form the embodiment 300 of FIG. 14, the enlarged portion 303 and cannula driven end 324 can be received together in the chuck of a driving apparatus, e.g., an MR-compatible compressed air drill. Engagement between the tab 326 and notch 310 further insures rotation of the trocar and cannula as one unit. The trocar/cannula 300 is suitable for guidance through localizer bores (60 in FIG. 2) to breast lesion sites because its axially symmetric facets, preferably rotated at high speed, e.g., 20–30,000 rpm, to enhance penetration, will minimize axial movement of surrounding tissue and structure, e.g., the cup 44, as it passes therethrough and minimize forces that would urge it from the bore axis as compared, for example, to a beveled needle that tends to be urged away from its bevel face as it passes through tissue.

The trocar/cannula 300 outer diameter is selected to be closely and rotatably received within the localizer bores (60 in FIG. 2). Indicia marks 338 may be added along the cannula to serve as indications of insertion depth within the localizer bores. These marks may also include numbers to indicate, for example, millimeter distances from the tip 332. To decrease penetration resistance, it may be preferable to create cutting edges by scooping the trocar facets 314. The enlarged portion 303 and cannula driven end 324 may define other shapes well known in the art for maximizing torque transfer thereto from the drill chuck, e.g., it could define a square cross section.

Once the tip 332 of the trocar has been positioned proximate to the lesion site, the trocar can be removed and the cannula 320 is suitably positioned for insertion of other instruments, e.g., a biopsy needle, a hook-wire or a laser fiber. In accordance with a feature of the trocar/cannula 300, the passage 322 of the positioned cannula is then substantially free of obstructing tissue.

Various equivalent structures can be used to lock the trocar and cannula together for penetration and yet allow subsequent withdrawal of the cannula. For example, in FIG. 15 another trocar embodiment 350 has a constant diameter and defines a tab 352 which is dimensioned to be received in a notch 354 defined in the driven end 356 of the cannula 360 of FIG. 16.

A prototype localizer has been fabricated in accordance with preferred embodiment 140 of FIG. 8 but without the bladder 150. The frame was formed of lucite with 2 millimeter diameter mineral oil filled lumens (mineral oil was used because no fat suppression sequences were anticipated). The array bores were 0.040 inch in diameter and spaced 5 millimeters apart. A phantom target cube of adiopose tissue having 5 millimeter sides was held within a larger (11×11×6 cm) foam phantom disposed within the frame.

The prototype was imaged within the head coil of a 1.5 Tesla system (Signa; GE Medical Systems, Milwaukee, Wis.) and spacings from the coordinate system rounded to the nearest 5 millimeters. Using these coordinates, a 19.5 gauge core-biopsy gun (Argon Medical, Athens, Tex.) was guided through bores selected in accordance with the imaged spacings and to a depth in accordance with the imaged spacings. One bore was selected in each of two different arrays. In each case, the needle tip was placed within the target and the biopsy gun fired to yield a small core.

From the foregoing, it should now be recognized that localizer embodiments have been disclosed herein especially suited for guidance of medical instrument tips to a breast lesion site in accordance with MR imaged spacings derived with the aid of MR visible coordinate systems. Additionally, trocar/cannula embodiments suitable for use with the localizer embodiments have been disclosed.

Embodiments in accordance with the invention offer several potential advantages. As particularly shown in embodiment 40 of FIG. 2, the cup 44 is selected to closely receive and support the patient's breast during both imaging and instrument guidance. Thus, the breast is not subjected to discomfort resulting from pressure or distortion as in some present stabilization techniques, e.g., compression between plates. Possible rupture or other damage to a breast implant is also avoided.

Because the breast is supported while in the localizer, the breast tissue is presented without compression to minimize interference with contrast dynamics and subsequent diagnostic interpretation. Also, relative movement between the breast and inserted markers (e.g., hook-wires, carbon trails) upon removal from the localizer should be reduced compared to compression techniques.

Again, because the breast is not subjected to pressure or distortion, normal spacing between multiple lesions is maintained. This may allow improved spatial selectivity of lesion treatments. For example, laser fibers can be directed specifically to each of two spaced lesions whereas, under breast compression, the lesions may be so close together that healthy tissue is also subjected to laser energy.

With embodiments of the invention, access to breast lesions may be obtained through each bore array. In addition to providing increased resolution of instrument placement and alternate routes to a lesion to avoid, for example, another proximate lesion, this feature also offers instrument guidance perpendicular to the chest wall, e.g., through bore array 54 of FIG. 2, which may be advantageous in reaching lesions near the chest wall.

Although embodiment lumens have generally been shown to be elongated, it should be understood that the teachings of the invention (and the definition herein of the term lumen) extend to lumens of other shapes and sizes that define a coordinate system, e.g., an elongated lumen between two end points could equivalently be replaced with small cylindrical lumens defining only the end points. It should also be understood that the term frame as used herein refers to an integral frame that defines elements such as lumens and bores as well as frames made up of a plurality of parts, some of which define these same elements.

The preferred embodiments have shown Cartesian coordinate systems with orthogonal bore arrays arranged orthogonally with these systems. It should be apparent, however, that the teachings of the invention extend to any coordinate system, e.g., polar, and any bore arrays that are arranged in operative association therewith, i.e., arranged to guide instrument tips proximate to points in a space defined by the coordinate system. Preferably, the bore arrays are arranged to make it easy for operators to use the imaging determined lesion spacings in selecting appropriate guide bores.

The preferred embodiments of the invention described herein are exemplary and numerous modifications, dimensional variations and rearrangements can be readily envisioned to achieve an equivalent result, all of which are intended to be embraced within the scope of the appended claims.

What is claimed is:

1. A magnetic resonance (MR) localizer for use with a medical instrument having a tip, comprising:
   at least one cup formed from a substantially MR transparent material to have a contour shaped and dimensioned to receive a breast therein;
   an MR visible coordinate system which serves to define points in an imaging space within the coordinate system having x, y, and z coordinate axes markers;
   means for positioning said at least one cup substantially within said imaging space; and,
   means for guiding the medical instrument to position the tip proximate to any chosen of said points.

2. The localizer of claim 1 wherein said positioning means includes a frame formed from a substantially MR transparent material and each of said markers includes a lumen and an MR signal-producing material within said lumen.

3. The localizer of claim 1 wherein
said positioning means includes a frame formed from a substantially MR transparent material; and,
said guiding means includes a first array of bores, each of said bores positioned in said frame.

4. The localizer of claim 3 wherein said guiding means further includes a second array of bores, each of said bores positioned in said frame and wherein said first and second arrays are spatially interleaved.

5. The localizer of claim 1 wherein said at least one cup has a flange and said positioning means includes a lip to abut said flange.

6. The localizer of claim 1 wherein said at least one cup has a wall including a plurality of apertures.

7. A method for localizing lesions in a breast with the aid of magnetic resonance (MR) imaging, comprising the steps of:
arranging an MR visible coordinate system which serves to define points in an imaging space within the coordinate system having x, y, and z coordinate axes markers;
substantially preventing movement of a breast positioned within said imaging space by the steps including fitting a cup formed from a substantially MR transparent material over said breast and holding said breast and said cup substantially fixed relative to said coordinate system;
MR imaging said coordinate system and a lesion within said breast to obtain the spacing therebetween;
selecting, in accordance with said spacing, one of a plurality of guide bores operatively arranged with said coordinate system; and,
inserting a medical instrument through the selected bore to place its tip proximate to said lesion.

8. The method of claim 7 wherein said fitting step includes the step of inserting an adhesive between said cup and said breast to reduce movement therebetween.

9. The method of claim 7 wherein said fitting step includes the step of inserting a medical grade adhesive between a flange of said cup and the chest wall surrounding said breast to reduce movement therebetween.

10. The method of claim 7 wherein said fitting step includes the steps of:
submerging said breast in a liquid to obtain a volumetric measure thereof; and
selecting said cup, in accordance with said volumetric measure, from a plurality of different sized cups.

11. The method of claim 7 wherein said inserting step includes the step of rotating said medical instrument with a drill.

12. A magnetic resonance (MR) localizer in combination with a medical instrument having a tip and an outer diameter, said localizer comprising:
at least one cup formed from a substantially MR transparent material to have a contour shaped and dimensioned to receive a breast therein;
an MR visible coordinate system which serves to define points in an imaging space within the coordinate system having x, y, and z coordinate axes markers;
means for positioning said at least one cup substantially within said imaging space;
means for guiding the medical instrument to position the tip proximate to any chosen of said points;
wherein said positioning means includes a frame formed from a substantially MR transparent material; and,
said guiding means includes a first array of bores, each of said bores positioned in said frame and having a bore axis, bore diameter, and bore length dimensioned to closely receive the outer diameter of the medical instrument in order to minimize the deviation of the tip from the bore axis when the medical instrument is passed through said each bore.

13. The combination of claim 12 wherein said guiding means further includes a second array of bores, each of said bores positioned in said frame and having a bore axis, bore diameter, and bore length dimensioned to closely receive the outer diameter of the medical instrument in order to minimize the deviation of the tip from the bore axis when the medical instrument is passed though said each bore and wherein said first and second arrays are spatially interleaved.

* * * * *